(12) United States Patent
Phillips et al.

(10) Patent No.: US 6,518,034 B1
(45) Date of Patent: Feb. 11, 2003

(54) TEST STRIP FOR BLOOD GLUCOSE DETERMINATION

(75) Inventors: Kevin J Phillips, Lancaster, SC (US); Gilbert W Cole, Charlotte, NC (US)

(73) Assignee: ABB Diagnostics, Ltd., Slough Berkshire (GB)

( * ) Notice: Subject to any disclaimer, the term of this patent is extended or adjusted under 35 U.S.C. 154(b) by 424 days.

(21) Appl. No.: 09/104,476

(22) Filed: Jun. 25, 1998

(51) Int. Cl.⁷ .................................................. C12Q 1/54
(52) U.S. Cl. ....................................................... 435/14
(58) Field of Search ............................. 435/14; 422/56, 422/57

(56) References Cited

U.S. PATENT DOCUMENTS

| | | | |
|---|---|---|---|
| 4,385,114 A | * | 5/1983 | Guthlein et al. ............... 435/28 |
| 4,900,449 A | | 2/1990 | Kraus et al. |
| 4,964,990 A | | 10/1990 | Kraus et al. |
| 5,076,935 A | | 12/1991 | Kraus et al. |
| 5,108,607 A | | 4/1992 | Kraus et al. |
| 5,128,171 A | * | 7/1992 | Gleisner .......................... 427/2 |
| 5,151,189 A | | 9/1992 | Hu et al. |
| 5,178,765 A | | 1/1993 | Hu et al. |
| 5,179,005 A | * | 1/1993 | Phillips et al. ................. 435/14 |
| 5,269,931 A | | 12/1993 | Hu et al. |
| 5,366,902 A | | 11/1994 | Cox et al. |
| 5,556,761 A | | 9/1996 | Phillips |
| 5,843,692 A | * | 12/1998 | Phillips et al. ................. 435/14 |

* cited by examiner

*Primary Examiner*—Ralph Gitomer
(74) *Attorney, Agent, or Firm*—Michael A Mann; Nexsen Pruet Jacobs & Pollard LLC

(57) ABSTRACT

A test strip for determining blood glucose concentration includes a test strip and a photometer. The test strip comprises a substrate formed with an aperture, a polymeric membrane adhered to the aperture and in registration with the aperture, having a quantity of reagent on its bottom surface of the membrane. The polymeric membrane is adhered to the bottom of the substrate by double sided tape. The placement of the reagent on the bottom surface of the membrane allows filtration of the red blood cells from plasma before the glucose in the blood reaches the reagent and carries with it oxygen to drive the glucose-reagent reaction to completion. The photometer includes an infrared LED for detecting glucose components in the reacted test strip and simple, one-button operation.

9 Claims, 3 Drawing Sheets

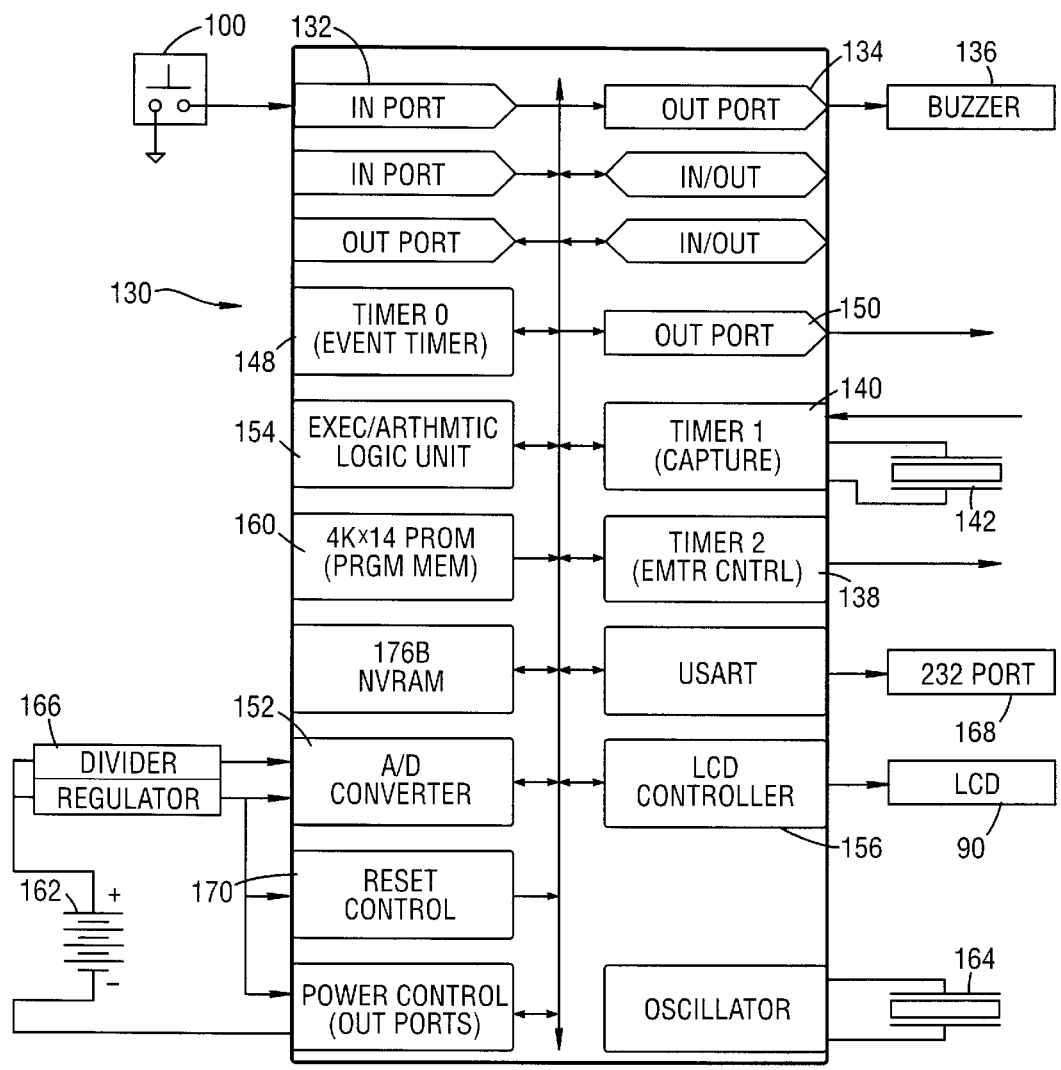

TEST STRIP FOR BLOOD GLUCOSE DETERMINATION

1. FIELD OF THE INVENTION

The present invention relates generally to blood glucose testing. In particular, the present invention advances a testing method and apparatus for use in determining blood glucose concentrations.

2. BACKGROUND OF THE INVENTION

The fast and accurate determination of one's blood glucose level is crucial to those with diabetes, especially for individuals who are insulin dependent. Failure to monitor blood glucose levels frequently and adequately can lead to severe health problems, diabetic coma, and, in some cases, death.

Given the importance of monitoring blood glucose levels, the prior art includes devices for self-monitoring. Self-monitoring permits diabetic patients to measure their own glucose level in a non-laboratory setting and at relatively low cost. Thus, self-monitoring improves the ability of diabetics, including those who have busy schedules and who travel frequently, to regulate their blood glucose levels.

The most prevalent form of self-monitoring employs a "test strip" and a photometer. A "test strip" is a substrate material that carries a reagent. The reagent is a chemical composition containing one or more chromophores that react chemically upon exposure to the analyte of interest, in this instance, glucose. When exposed to glucose present in blood plasma, the chromophores change color, with the degree of color change being a function of the glucose concentration.

A conventional photometer is a hand-held electronic device that measures the quantity of light reflected from a particular body. The reflected light measured by the photometer translates by programming into a glucose concentration value using reference data that relates glucose concentration as function of reflectance for a particular chromophore. The photometer also displays the glucose level in mg/dL using a liquid crystal display or light-emitting diode.

In use, a patient will place a small sample of his blood on a defined area of a test strip containing the reagent composition. Typically, the individual will be required to wait a predetermined number of seconds before removing excess blood from the surface of the test strip.

The test strip is then inserted into the photometer. After another predetermined period of time, the photometer will display the results of the glucose measurement. More recent systems do not require the user to wipe excess blood and thus are called "non-wipe" systems.

Other "non-wipe" self monitoring systems measure blood glucose levels as a function of electrical resistance rather than color change of a reagent. In these systems, a "Wheatstone bridge" is utilized instead of a photometer. A Wheatstone bridge is a four-arm bridge circuit which measures an unknown electrical resistance, which in this instance is the resistance of the blood glucose which varies with concentration. In use, an individual places a quantity of blood onto an impermeable substrate and in doing so, completes the bridge circuit.

Despite the fact that non-wipe systems are superior to their predecessors in both accuracy and convenience, present day non-wipe systems do not consistently yield results that are as accurate as clinical measurements. Although the American Diabetes Association has stated that self-monitoring systems should produce readings within 15% of the actual glucose level, present day self-monitoring systems fall short of that level of accuracy. Self-monitoring systems fail to yield consistently accurate results for several reasons, including variation in the thickness of the reagent composition, inhomogeneity of the reagent composition, insufficient oxygen for driving the reaction between the reagent composition and the blood, poor separation of red blood cells from plasma, and thermal degradation of the enzymes within the reagent composition during the bonding of the reagent to the substrate.

Thus, there exists a need for a blood glucose testing method and apparatus that is inexpensive and easy to use but consistently yields clinically accurate glucose concentration values.

SUMMARY OF THE INVENTION

According to its major aspects and briefly stated, the present invention is a testing method and apparatus, including test strip and photometer for use in measuring the concentration of blood glucose levels. The test strip comprises a substrate to which is adhered a polymeric membrane having a quantity of reagent composition applied on the side of the membrane opposite the side that is adhered to the substrate. The arrangement of the elements of the test strip is very important. The polymeric membrane, preferably a polyethersulfone or acetate membrane having a porosity between approximately 250 and 1200 microns, is centered on an aperture formed in the substrate. Double-sided tape is used to adhere both the membrane and the reinforcing layer to the substrate.

The photometer of the present invention uses infrared light to determine blood glucose. The amount of light reflected by the reacted components from the drop of blood on the test strip is converted to a blood glucose value and displayed. Additionally, the meter has built-in tests to determine if the reaction has failed to go to completion or the value determined is outside the nominal range of the meter. In addition, the meter has a number of features to make it easier to use.

A droplet of blood is placed in the aperture of the substrate and, when its plasma has migrated through the membrane and reacted with the reagent, infrared light is directed to the reagent side of the membrane for reflectance analysis. The substrate is preferably made of polyvinyl chloride in a neutral white or light gray color that preserves the integrity of the photometry and occludes stray light, and provides structural support to the membrane.

The reagent composition is applied only to the surface of the polymeric membrane and then heated to a temperature no greater than 129° F. for an exposure period of time of no longer than 20 minutes to adhere the reagent composition to the surface of the membrane, rather than allow it to soak into the membrane. Reagent-free pores in the membrane enable them to perform a mechanical separation of plasma from red blood cells that would otherwise adversely affect a photometric analysis based on reflectance of red or infrared light. Keeping the pores substantially free of reagent also enables them to deliver the oxygen needed for the reaction between blood glucose and the reagent.

Accordingly, a major feature of the present invention is the specific location of the membrane placed on the substrate. The membrane is placed between the substrate and the reagent. When a sample of blood is deposited on the top of the membrane through the aperture in the substrate, the size of the membrane pores traps the red blood cells but enables the plasma to migrate through the membrane. As a consequence, the blood which contacts and subsequently reacts with the reagent is relatively free of red blood cells. Filtering red blood cells from the blood sample prior to contact with the reagent minimizes the occurrence of incomplete reactions or reaction gradients, which in turn results in more accurate blood glucose readings.

In addition, the surface of the membrane is air permeable and therefore permits air to contact the reagent composition. This air, and oxygen in particular, serves to drive the reaction between the blood and the reagent composition to completion, and thus maximizes the accuracy of the resulting blood glucose reading.

Another major feature of the present invention is the use of infrared light to detect the changes in the reagent when it has been exposed to the blood components. A non-visible type of light minimizes the influence of visible light in the photometry but, only when red blood cells have been separated from the glucose component of the plasma can infrared light be practical to use.

Other features and advantages will be apparent to those skilled in the art from a careful reading of the Detailed Description of a Preferred Embodiment accompanied by the following drawings.

BRIEF DESCRIPTION OF THE DRAWINGS

In the drawings,

FIG. 5 illustrates a controller circuit block diagram according to a preferred embodiment of the present invention; and

DETAILED DESCRIPTION OF A PREFERRED EMBODIMENT

The present invention is an apparatus and method for blood glucose monitoring. The apparatus includes a test strip and photometer and, in particular, a photometer that does not require excess blood to be wiped from the test strip and which uses infrared light reflectance to measure the concentration of glucose in blood. Use of this test strip and photometer for blood glucose measurements yield blood glucose concentration readings which fall within 15% of the correct blood glucose level 95% of the time, and within 20% of the true glucose level 100% of the time.

Figure 1:
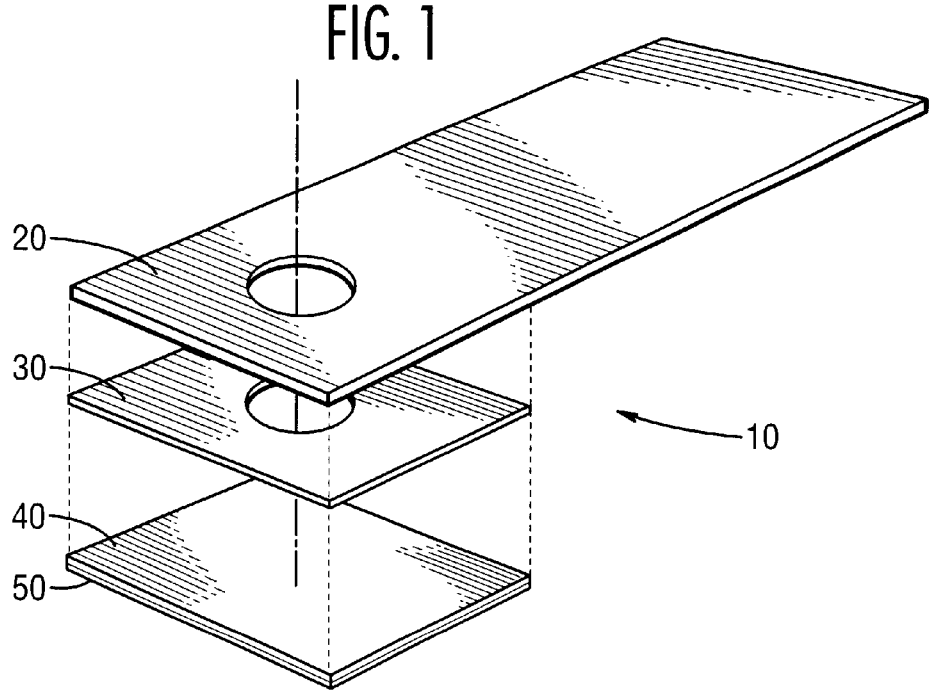
FIG. 1 is an exploded top view of blood glucose test strip according to a preferred embodiment of the present invention.
Figure 2:
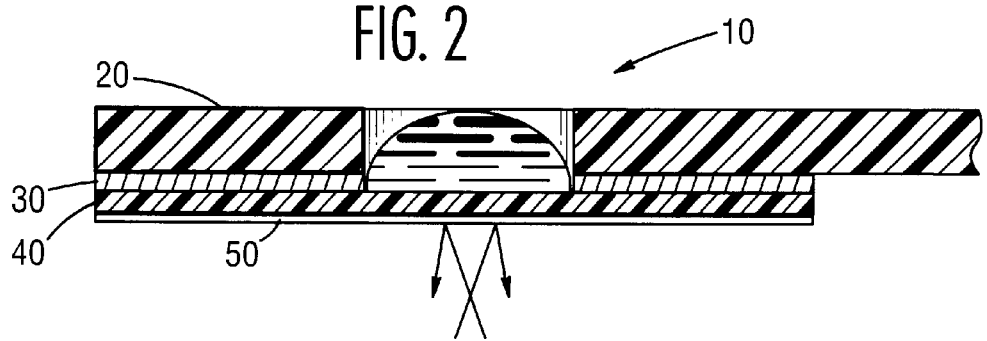
FIG. 2 is a cross sectional view of the test strip according to a preferred embodiment of the present invention.

Referring now to FIGS. 1 and 2, there is shown an exploded view of a blood glucose test strip according to a preferred embodiment of the present invention and generally designated by reference numeral 10. In the preferred embodiment shown, test strip 10 comprises a substrate 20, a tape layer 30 and a polymeric matrix membrane 40 carrying a layer of reagent 50. As noted above, the arrangement of these elements is critical to the successful functioning of the test strip. In particular, the drop of blood is deposited on one side of test strip 10 and the light for the photometric analysis is directed at the opposite side of strip 10. The elements of the test strip 10 are arranged with this orientation in mind.

An aperture 22 is formed in substrate 20 near one end for receiving a small droplet of blood 70. Substrate 20 has a top surface 24 and a bottom surface 26 and may be any shape and size necessary to permit operation with the optical element of the photometer (not shown) it is intended to be used with. Preferably, however, aperture 22 is circular in shape with a diameter of approximately 0.201 inches ±0.003 inches so that a small droplet of blood can quickly fill aperture 22 and so that the user can more easily correlate the amount of blood needed to the amount of blood issuing from a finger prick by the apparent diameter of aperture 22 that receives the droplet. When the diameter of the blood droplet on the user's finger is the same size or larger than the diameter of aperture 22, enough blood is available for analysis.

Substrate 20 may be made of any polymeric or cellulosic material possessing the requisite rigidity to enable its insertion into a photometer. Preferably, given the considerations of both cost and strength, substrate 20 is made of polyvinyl chloride (PVC) and is 2.125±0.005 inches long by 0.630±0.005 inches wide by 10 mills thick. Substrate 20 is opaque and made in a color that does not interfere with the photometry of the photometer, such as pantone 420C.

A thin layer 30 of double-sided tape, that is, tape with adhesive on both sides so that other layers can be adhered to both sides of the tape, is used to adhere to substrate 20 to a top surface 42 of membrane 40. Any adhesive that binds the elements together will suffice, however.

Polymeric membrane 40 also has a bottom surface 44. Reagent 50 is applied to bottom surface 44, that is, a surface of membrane 40 opposite that which will be adhered to substrate 20. Membrane 40 has a columnar pore structure with a porosity of between 250 microns and 1200 microns. Preferably, the porosity of membrane 40 is approximately 450 microns. Membrane 40 should be larger than aperture 22 of substrate 20, so the upper surface 42 at the perimeter of membrane 40 adheres to bottom surface 26 of substrate 20, and have a thickness of about five mills. If aperture 22 is 0.201±0.003 inches in diameter, then membrane 40 is preferably 0.250±0.001 inches in diameter. A suitable polymeric membrane 40 is made of polyethersulfone and sold under the trademark MICRON PES by Micron Separations Incorporated. This membrane is well known and is the subject of the following U.S. Pat. Nos. 4,900,449; 4,964,990; 5,076,935; and 5,108,607. Acetate also makes a suitable membrane.

Reagent 50 may be any chemical or enzymatic composition of a specific viscosity of 1500–2000 centipoise normally used to detect blood glucose concentrations. A preferred reagent 50 comprises one or more chromophores and one or more enzymes. The chromophore is preferably 3, 3', 5, 5' tetramethyl benzidine. The enzymes may be glucose oxidase and peroxidase. The enzymes and chromophores, which are the active ingredients of reagent 50, are suspended in a polymeric matrix of polymer resin emulsion of vinyl acetate ethylene copolymer and polyvinyl acetate. This preferred reagent composition is the subject of U.S. Pat. No. 5,556,761 issued to Phillips, which is incorporated herein by reference. Reagent 50 of a specific viscocity of 1500–2000 centipoise is applied to membrane 40's bottom surface 44 side and then cured so that it remains essentially on the surface and does not soak in or saturate membrane 40. Thus the interior of membrane 40 is substantially free of reagent.

The assembly of test strip 10 first involves the application of a layer of reagent 50 to bottom surface 44 of membrane 40 using any technique commonly employed in the art. The layer of reagent composition 50 preferably has a thickness of approximately 0.001 inches. The size of reagent composition 50 should be greater than the diameter of aperture 22. Membrane 40 and reagent composition 50 are then subjected to a preselected thermal schedule. The precise maximum temperature to which membrane 40 and reagent composition 50 are exposed will depend upon the particular chemical composition of reagent 50 and will therefore require a modest amount of experimentation common to those with ordinary skill in the art. When reagent 50 is a compound disclosed in U.S. Pat. No. 5,556,761, the maximum temperature should not exceed 129° F. for an exposure period of time of no longer than 20 minutes. Thereafter, membrane 40 is placed in registration with aperture 22 and adhered to substrate using tape 30.

It will be clear from the foregoing that the drop of blood 70 must be deposited on one side of test strip 10 and light must impinge on the other side so that there is a separation of red blood cells on the one side of membrane 40 from the reacted reagent 50 on the other. It is also important that, to obtain accurate results, tight tolerances are required. The more important of these tolerances are the thickness of reagent 50, the thickness of membrane 40 (which governs the speed of plasma from blood deposition to reaction).

Figure 3:
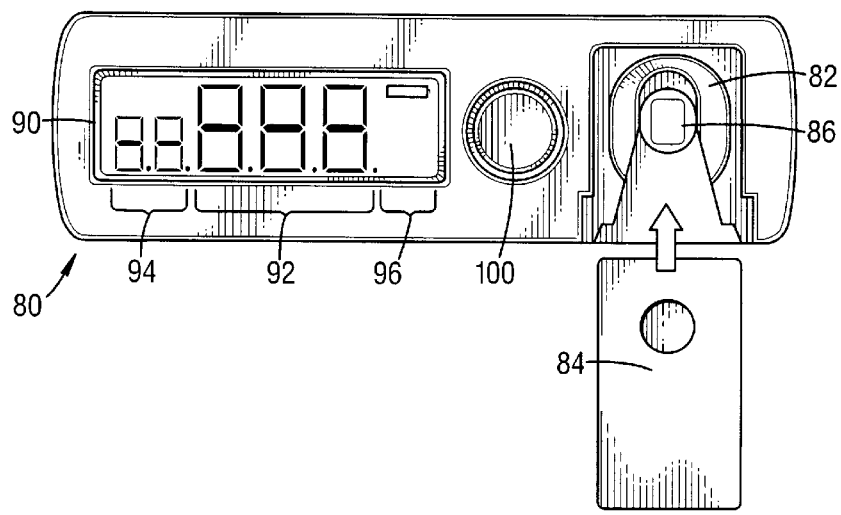
FIG. 3 is a top view of a photometer according to a preferred embodiment of the present invention.

FIG. 3 illustrates a top view of a photometer 80 according to a preferred embodiment of the present invention. Photometer 80 includes a well area 82 where a test strip 84 is inserted when a test or calibration is to be performed. Near the center of well area 82 is a reaction pad 86, where light will strike test strip 84. Photometer 80 has a display 90 with a number of fields: a first field 92 displays the glucose value or remaining time until an analysis will be completed; a second field 94 displays alternatively the memory location and function; a third field 96 displays the units for the glucose value and remaining time; and a fourth field 98 displays the low battery icon. Also there is a multi-function control button 100 that, by holding it down for various intervals, will scroll through a series of functions or through the values associated with those functions, as will be explained in more detail below. Display 90 is a liquid crystal display.

Figure 4:
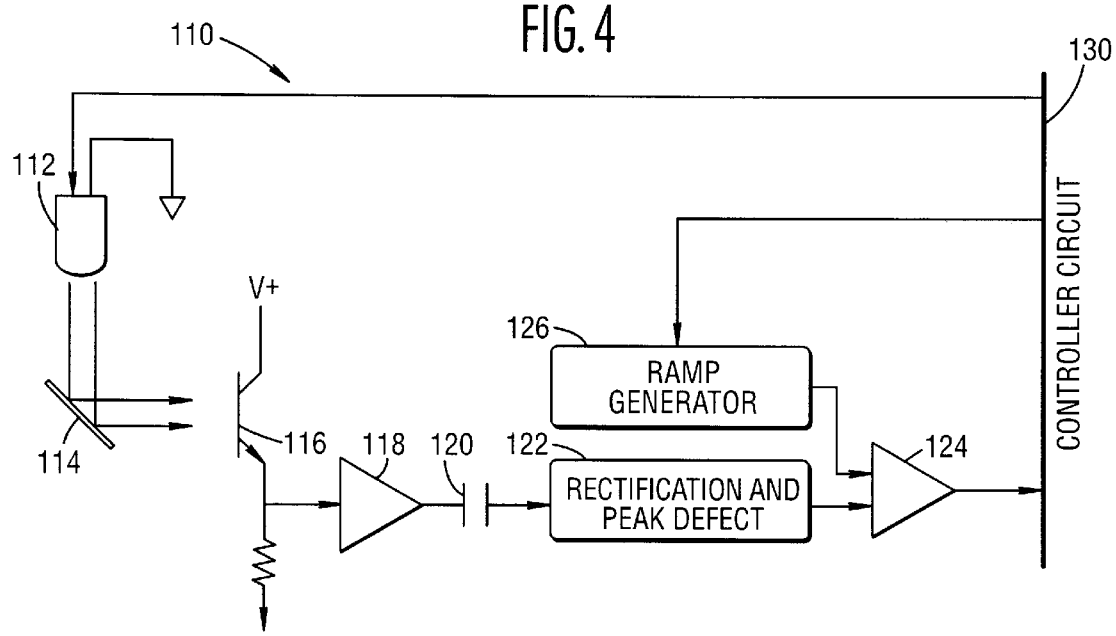
FIG. 4 illustrates a reflectance conversion circuit according to a preferred embodiment of the present invention.

FIG. 4 is a schematic illustration of the reflectance conversion circuit 110. The purpose of this circuit is to convert light energy reflected off the membrane of test strip 84 at the reflecting plane to a repeatable output. The output provided by this conversion circuit is a pulse having a duration proportional to the amount of reflected light energy received by a photoresistor poised to receive that reflected light. An enabling signal to an infrared light emitting diode 112 comes from a controller circuit 130 that will be described in more detail presently. This signal causes diode 112 to emit light, preferably centered on a wavelength of 880 nm and emited as diffused light, toward a reflecting plane 114 where the test strip membrane has been positioned. When light is reflected by plane 114, it generates an electrical current in a photo-resistor 116 from the reflected light. The voltage drop across photoresistor 116 is output for amplification by a preamplifier 118 and filtration by a capacitor 120.

The signal is then rectified and its peak (direct current) detected by a reactification and peak detection module 122. The peak dc output is fed to the "B" side of a comparator 124. To the "A" side of comparator 124 is fed a gradually increasing, "ramped" signal from a ramp generator 126. Comparator 124 sends a pulse to controller circuit 130 a short interval after infrared LED 112 fires. That pulse ends when the output of ramp generator 126 exceeds the peak signal from module 122. Therefore, the higher the peak signal, the longer will be the pulse. The pulse from ramp generator 126 is delayed slightly from the enabling signal from controller circuit 130 in order to allow the B side peak voltage to stabilize and to assure that the timing of the pulse is consistent and proportional with peak voltage. A counter in control circuit 130 resets as soon as ramp generator 126 is fired in order to get an accurate pulse length measurement.

FIG. 5 illustrates a block diagram of controller circuit 130 which is preferably a microcircuit unit. Controller circuit 130 consists of all the hardware outside conversion circuit 110. This circuit provides the signal interfacing, computation, logic sequencing, and data traffic control required to interface with the conversion circuit to convert the reflectance values to blood glucose concentration values and the implement the meter's user interface.

Pressing control button 100 produces an output signal at input port 132 that is forwarded from an output port 134 to a piezoelectric buzzer or beeper 136 to signal that the results of the measurement are available, an error has occurred or that the user needs to take an action. Push button 100 is a normally open push button that is pulled up at the controller circuit input port. All meter-user control functions are performed with control button 100. Buzzer 136 outputs sounds at a fixed frequency and volume but varying duration. For example, one long beep indicates that there is an error; three short beeps indicates an measurement has been completed.

A first timer 148 is used as an event timer. Preferably an 8-bit timer with 8-bit prescaler, timer 148 generates a periodic interrupt to time meter events such as the control button holddown time and the concentration measurement countdown. A second timer 140 is preferably a 16-bit timer/counter that measures the width of the pulse from conversion circuit 110 using an external crystal 142 as a timing base. The capture capability of second timer 140 captures the count value at the trailing edge of the pulse from conversion circuit 110. As soon as the pulse toggle is detected, second timer 140 stops counting.

A third timer 138 controls power emitted to conversion circuit 110. When enabled, third timer 138, preferably an 8-bit timer, generates a square wave.

A logic unit 154 contains a 35-instruction processing unit for the execution of the software that performs the meter calculations and control functions.

Controller circuit 130 contains two memories. There is a first memory 144 that is a programmable read only memory for storing the control program. First memory 144 also stores the coefficients used for reflectance-to-glucose concentration calculation, the measurement of countdown time, and other fixed data of meter 80. There is a second memory 146, a non-volatile radom access memory for temporary storage of program variables, stacks, scratch pad, etc., that will be used by the program software. This memory will also store the 40 most recently determined glucose measurement values. First memory 144 will hold measurements without battery power but second memory 146 will not.

Controller circuit 130 is operated by a battery 162 and uses an oscillator 164 separate from oscillator 142 for sequence processing. Battery 162 comprises preferably three silver oxide, 357 button-type batteries. A divider/regulator circuit 166 regulates the power supply and indicates low power. Also, an RS-232 serial port 168 is provided to upload calibration strip measurements to an external device during production testing.

Controller circuit 130 has an on-board liquid crystal display controller 156 that provides the proper voltage and timing sequence for display 90. Controller 156 controls 32 segments and 4 commons.

Controller circuit has an analog-to-digital converter 152, preferably 8-bit, with a five-to-one input multiplexing capability for determining low battery. There is also a reset control 170 to control the reset when fresh batteries are installed. Reset control 170 holds the controller circuit 130 in reset state until input power and the oscillators stabilize. Then reset controller vectors to a reset subroutine allowing complete initialization and configuration of the meter under software control.

In operation, control button 100 is pressed and released to turn meter 80 on. After a self-test to check for battery power and to verify that the memory, logic unit, timer and display are operational, meter 80 determines how long button 100 has been pressed. If button 100 is held less than two seconds, meter 80 will emit a short beep and then is ready perform a measurement. If button 100 is held more than two seconds, it begins to scroll through four functions: memory, units, correction factor, measurement. Each additional two seconds that button 100 is held, meter 80 will scroll from function to function until button 100 is released. To reach the final function, change of units, the user needs to hold button 100 for three seconds.

For a measurement, meter 80 counts down through a predetermined number seconds (preferably less than 60) in order to allow blood on test strip 84 to migrate through the membrane and react with the reagent at reaction pad 86. Then conversion circuit 110 will generate a pulse proportional to the concentration of glucose in the sample, determine the width of the pulse using controller circuit 130 and apply a correction factor that depends on the particular test strip 84. This correction factor involves the addition of increments of 3.33% to the measured glucose value added or subtracted from the nominal value based on an indicator number ranging from 1–15, with 8 being the nominal indicator number. When the measurement results are displayed, the beeper will emit three short beeps to alert the user. The measurement will then be stored in memory if button 100 is pressed after measurment is displayed once released.

For a calibration measurement, the user presses the control button a second time after the countdown. When the results of the measurement are displayed, three short beeps are heard, a "CL" is displayed along with it to indicate a calibration measurement. Calibration measurements are not stored in memory and no correction factor is applied.

Pressing button 100 for two seconds or continuing to hold it for yet an additional two seconds, will scroll display 90 to the correction factor to be applied. If the button is released when the code is displayed, then by pressing button 100 again in a series of short pulses, meter 80 will increment the code through the range of values from 1–15.

If button 100 is held for more than two seconds, it will display the memory. By releasing button 100 and then pressing in momentarily and repeatedly, it will scroll through the measurements in memory. Continuing to hold button 100 for an additional two seconds or pressing it again for three seconds will cause photometer 80 to display the measurement units selected. Release of button 100 and then pressing button 100 briefly will alternate between units of "mg/dl" and "mmol/l".

To determine the concentration of glucose present in a sample of blood, test strip 10 is inserted into the photometer. A drop of blood 70 is placed in aperture 22 on top surface 42 of membrane 40, and photometer 80 is activated by pressing button 100. The plasma portion of the blood will be absorbed by membrane 40 and travel through it toward reagent composition 50. As the blood migrates, the porosity of membrane 40 (approximately 450 microns) results in a filtering action such that red blood cells (>450 microns) will become trapped above membrane 40, while plasma cells (<450 microns) will travel through membrane 40 and subsequently contact reagent 50 on bottom surface 44. In addition, the porosity of membrane 40 enables oxygen to travel through membrane 40 and contact reagent 50, and consequently drive the reaction between the plasma cells and reagent 50. The presence of sufficient oxygen afforded by the porosity of polymeric membrane 40 increases the rate of reaction between the plasma and reagent 50 and therefore enables a more efficient and accurate glucose concentration determination.

It will be apparent to those skilled in the art of glucose testing that many modifications and substitutions can be made in the preferred embodiments described herein without departing from the spirit and scope of the present invention, defined by the appended claims.

What is claimed is:

1. A test strip for use with a photometer for determining blood glucose concentration from a blood sample, said strip comprising:

a substrate having a top surface and an opposing bottom surface, said substrate having an aperture formed therethrough, said aperture being adapted to receive and receiving a droplet of blood;

a porous membrane having a top surface and an opposing bottom surface, said top surface of said membrane adhered to said bottom surface of said substrate so that said membrane is in registration with said aperture in said substrate, said porous membrane filters red blood cells from plasma in said blood; and a reagent carried on said bottom surface of said membrane, the interior of said membrane being substantially free of said reagent, said reagent reacts with glucose in blood plasma.

2. The test strip as recited in claim 1, wherein said membrane is made of a polymeric matrix having columnar pores.

3. The test strip as recited in claim 1, wherein said membrane has a pore size larger than 0 microns and less than 1200 microns.

4. The test strip as recited in claim 1, wherein said membrane is made of a material selected from the group consisting of polyethersulfone and acetate.

5. The test strip as recited in claim 1, wherein said substrate is pantone 420C.

6. The test strip as recited in claim 1, wherein said reagent includes at least one chromophore and at least one enzyme.

7. The test strip as recited in claim 6, wherein said enzyme include glucose oxidase and peroxidase.

8. The test strip as recited in claim 1, wherein said reagent includes 3, 3', 5, 5' tetramethyl benzidine.

9. The test strip as recited in claim 1, wherein said reagent includes 3, 3', 5, 5' tetramethyl benzidine, glucose oxidase and peroxidase suspended in a polymeric matrix of polymer resin emulsion of vinyl acetate ethylene copolymer and polyvinyl acetate.

\* \* \* \* \*